(12) United States Patent
Van Immerseel et al.

(10) Patent No.: US 10,420,745 B2
(45) Date of Patent: Sep. 24, 2019

(54) COMPOSITION INHIBITING GRAM-POSITIVE, PATHOGENIC BACTERIA

(71) Applicant: PERSTORP AB, Perstorp (SE)

(72) Inventors: Filip Van Immerseel, Eke (BE); Karolien Van Driessche, Zele (BE); Richard Ducatelle, Wortegem-Petegem (BE); Conrad Gerard Schwarzer, Beringen (BE)

(73) Assignee: PERSTORP AB, Perstorp (SE)

( * ) Notice: Subject to any disclaimer, the term of this patent is extended or adjusted under 35 U.S.C. 154(b) by 0 days.

(21) Appl. No.: 15/562,105

(22) PCT Filed: Mar. 17, 2016

(86) PCT No.: PCT/SE2016/000012
§ 371 (c)(1),
(2) Date: Sep. 27, 2017

(87) PCT Pub. No.: WO2016/159853
PCT Pub. Date: Oct. 6, 2016

(65) Prior Publication Data
US 2018/0071241 A1   Mar. 15, 2018

(30) Foreign Application Priority Data

Mar. 27, 2015 (SE) ...................... 1500157

(51) Int. Cl.
| | | |
|---|---|---|
| *A61K 31/225* | (2006.01) | |
| *A23K 20/158* | (2016.01) | |
| *A23K 20/105* | (2016.01) | |
| *A23K 50/75* | (2016.01) | |
| *A61K 31/22* | (2006.01) | |
| *A61P 31/04* | (2006.01) | |
| *A61K 47/02* | (2006.01) | |
| *A61K 31/122* | (2006.01) | |

(52) U.S. Cl.
CPC .......... *A61K 31/225* (2013.01); *A23K 20/105* (2016.05); *A23K 20/158* (2016.05); *A23K 50/75* (2016.05); *A61K 31/122* (2013.01); *A61K 47/02* (2013.01); *A61P 31/04* (2018.01)

(58) Field of Classification Search
CPC .... A61K 31/22; A61K 31/225; A23K 20/105; A23K 20/158; A23K 50/75; C11C 3/02
See application file for complete search history.

(56) References Cited

U.S. PATENT DOCUMENTS 5,658,595 A   8/1997   Van Os

FOREIGN PATENT DOCUMENTS

| CN | 101658240 A | * | 3/2010 | | |
|---|---|---|---|---|---|
| EP | 2215913 A1 | | 8/2010 | | |
| EP | 2294929 A1 | | 3/2011 | | |
| WO | 2006/085346 A1 | | 8/2006 | | |
| WO | 2010/106488 A2 | | 9/2010 | | |
| WO | WO-2010106488 A2 | * | 9/2010 | ............ | C11C 3/025 |
| WO | 2011/002298 A2 | | 1/2011 | | |
| WO | WO-2011002298 A2 | * | 1/2011 | ........... | A23K 20/158 |

OTHER PUBLICATIONS

Sutter, Marc et al., "1-O-Alkyl (di)glycerol ethers synthesis from methyl esters and triglycerides by two pathways: catalytic reductive alkylation and transesterification/reduction," Green Chemistry, 2013, 15, pp. 786-797.
Berger, Matthias et al., "Enzymatic Esterification of Glycerol II. Lipase-Catalyzed Synthesis of Regioisomerically Pure 1(3)-rac-Monoacylglycerols," Journal of American Oil Chemists' Society, vol. 69, No. 10, Oct. 1992, pp. 961-965.
Timbermont, L. et al., "Control of Clostridium perfringens-induced necrotic enteritis in broilers by target-released butyric acid, fatty acids, and essential oils," Avian Pathology, Apr. 2010, 39(2), pp. 117-121.
Doty, D.M., "*Salmonella* Destroyed by Some Simple Chemicals," Fats, and Proteins Research Foundation, Inc., Apr. 23, 1968, No. 46, pp. 1-2.
Namkung, H. et al., "Antimicrobial activity of butyrate glycerides toward *Salmonella typhimurium* and Clostridium perfringens," Poultry Science, 2011, No. 90, No. 10, pp. 2217-2222.
International Search Report and Written Opinion dated Jun. 21, 2016 issued in corresponding International Application No. PCT/SE2016/000012.

\* cited by examiner

*Primary Examiner* — Timothy P Thomas
*Assistant Examiner* — George W Kosturko
(74) *Attorney, Agent, or Firm* — Polsinelli PC

(57) ABSTRACT

The present invention refers to a glycerol ester composition comprising the reaction product obtained from reacting valeric acid and glycerol at a molar ratio of between 1:0.8 and 1:1.2, for use in reduction and/or inhibition of the growth of gram-positive, pathogenic bacteria. The present invention also refers to said glycerol ester composition for use in prevention and/or alleviation of necrotic enteritis in the gastric tract of galloanserans.

12 Claims, 1 Drawing Sheet

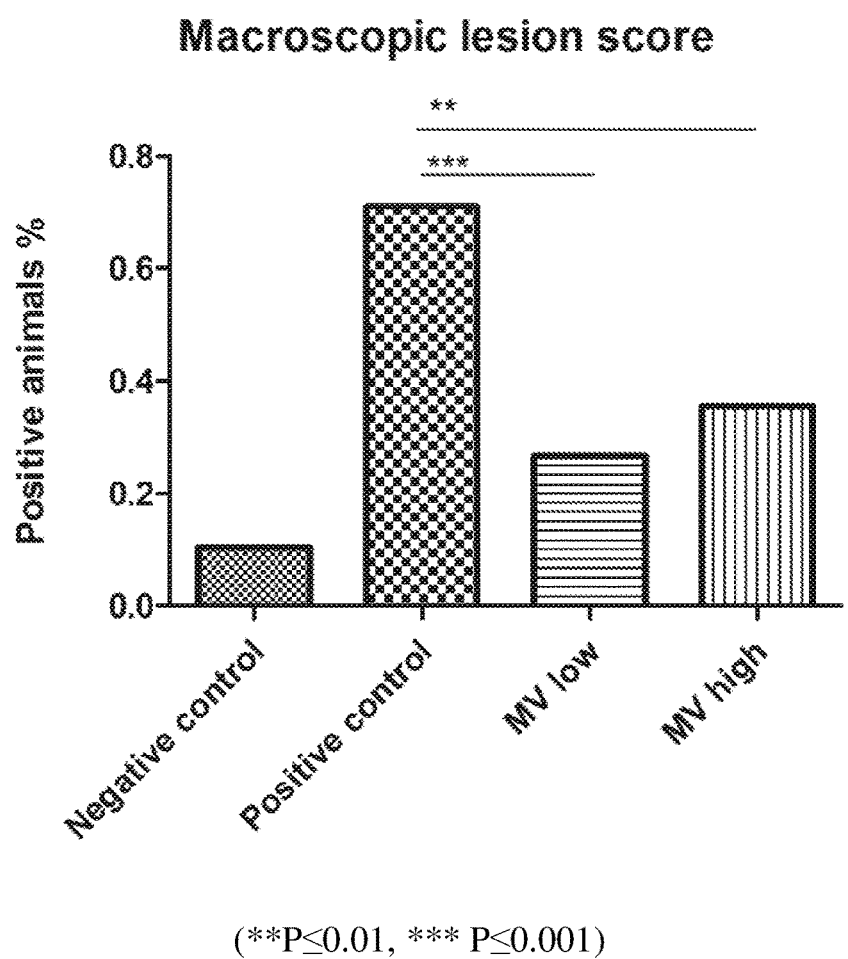
(P≤0.01, * P≤0.001)

COMPOSITION INHIBITING GRAM-POSITIVE, PATHOGENIC BACTERIA

RELATED APPLICATIONS

This application is a national stage application (under 35 U.S.C. § 371) of PCT/SE2016/000012, filed Mar. 17, 2016, which claims benefit of Swedish application SE1500157-1, filed Mar. 27, 2015, which are both incorporated herein by reference in their entireties.

FIELD OF THE INVENTION

The present invention refers to a glycerol ester composition comprising the reaction product obtained from reacting valeric acid and glycerol at a molar ratio of between 1:0.8 and 1:1.2, for use in reduction and/or inhibition of the growth of gram-positive, pathogenic bacteria. It also refers to said glycerol ester composition for use in prevention and/or alleviation of necrotic enteritis in the gastric tract of galloanserans.

BACKGROUND OF THE INVENTION

Gram staining differentiates bacteria by the chemical and physical properties of their cell walls by detecting peptidoglycan, which is present in a thick layer in gram-positive bacteria. In a Gram stain test, gram-positive bacteria retain the crystal violet dye, while a counterstain (commonly safranin or fuchsine) added after the crystal violet gives all gram-negative bacteria a red or pink coloring.

Among the gram-positive bacteria are the genera *Clostridium, Listeria, Bacillus, Staphylococcus* and *Streptococcus*, which are all pathogenic in humans. The genus *Clostridium* contains around 100 species that include common free-living bacteria, as well as important pathogens.

One of the *Clostridium* species, *Clostridium perfringens*, is a ubiquitous spore-forming pathogen that produces at least 15 different potent toxins that are responsible for severe diseases in humans and animals (Popoff and Bouvet, 2009).

*C. perfringens* causes a wide range of symptoms in humans, from food poisoning to gas gangrene, which is necrosis, putrefaction of tissues, and gas production. The gases form bubbles in muscle (crepitus) and the characteristic smell in decomposing tissue. After rapid and destructive local spread (which can take only hours), systemic spread of bacteria and bacterial toxins may cause death. This is a problem in major trauma and in military contexts.

It is generally accepted that *C. perfringens* toxinotype A is the cause of several different diseases in broiler chickens, including clinical necrotic enteritis, which is characterized by outbreaks of spiking mortality. This classical acute clinical form of necrotic enteritis has emerged in broilers in the European Union following the ban on antimicrobial growth promoters in animal feed in 2006 (Van Immerseel et al., 2009). Many animals die without premonitory signs, and mortality can, in some cases, rise up to 50% (Wijewanta and Senevirtna, 1971).

*Clostridium perfringens*, however, also can cause an unapparent infection or a subclinical disease characterized by the presence of small ulcerative lesions in the mucosa of the small intestine. It is generally accepted that these small intestinal lesions lead to poor digestion and absorption. Moreover, multifocal liver lesions can be found during meat inspection at slaughter. These red or white foci are due to colonization of the liver by high numbers of *C. perfringens*, resulting in multifocal cholangiohepatitis (Kaldhusdahl and Hofshagen, 1992).

All of these lesions result in reduced weight gain and increased feed conversion ratio (Kaldhusdahl et al., 2001). Feed conversion ratio is defined as the ratio of feed mass input to body mass output. The economic impact of subclinical necrotic enteritis is considered to be much more important than that of clinical necrotic enteritis. It has been suggested that subclinical necrotic enteritis would occur in 20% of the broilers. This results in an increase in feed conversion rate of 10.9%, having a severe economic impact.

Worldwide, necrotic enteritis is probably one of the most widespread enteric diseases in poultry, with considerable consequences for the performance of affected flocks. It can present as a sudden increase in mortality or as an insidious subclinical disease. The indication of necrotic enteritis is the presence of necrotic lesions in the small intestinal mucosa. The diagnosis of necrotic enteritis is made at necropsy.

Besides causing both severe health issues among affected animals and great economical losses, pathogens like *Clostridium perfringens* can also be spread from infected animals to humans. People handling these animals or consumers of the animals or animal products risk getting infected and, as described above, develop serious illness.

The emerging problem with antimicrobial resistance resulted in the ban of growth promoting antibiotics in the European Union in 2006. This calls for new, alternative methods to counteract pathogenic bacteria in both humans and animals.

It is well known in the art that various short chain fatty acids as well as their respective glycerol monoesters have antibacterial properties. There are several benefits associated with distributing the short chain fatty acids as glycerol esters. Glycerol esters are less corrosive than the corresponding free acids, facilitating handling and transportation of the products. Some of the short chain fatty acids, like for example butyric acid and valeric acid, have a very unpleasant smell. The corresponding glycerol esters of these acids are more or less odorless. Additionally, glycerol esters bind the short chain fatty acids, enabling them to reach further down in the gastrointestinal tract of a human or an animal before being adsorbed to the bloodstream.

Quite a lot of studies have been published on the use of glycerol esters of propionic acid and butyric acid as antibacterial agents. However, the specific antibacterial action of glyceryl monovalerate has not been described.

The present invention shows that glyceryl monovalerate is much more effective than either glyceryl monopropionate or glyceryl monobutyrate for reducing and/or inhibiting the gram-positive bacterium *Clostridium perfringens* in vitro. The antibacterial action of glyceryl monovalerate against *Clostridium perfringens* is confirmed in an in vivo study on broiler chicken.

BRIEF DESCRIPTION OF THE DRAWING

The FIG. is a graph showing the percentage of positive chicken (with macroscopic lesion score≥2).

DETAILED DESCRIPTION OF THE INVENTION

The present invention refers to a glycerol ester composition comprising the reaction product obtained from reacting valeric acid and glycerol at a molar ratio of between 1:0.8 and 1:1.2, for use in reduction and/or inhibition of the growth of gram-positive, pathogenic bacteria. In the context of the present invention, pathogenic is to be understood as causing clinical or subclinical disease in a wide range of species, like for example in galloanserans and/or in humans. The gram-positive, pathogenic bacteria whose growth is reduced and/or inhibited by the glycerol ester composition according to the present invention can, for example, be of the genera *Clostridium, Listeria* and/or *Bacillus*. In particular, growth of the gram-positive bacterium *Clostridium perfringens* is reduced and/or inhibited by the use of said glycerol ester composition.

The present invention also refers to a glycerol ester composition comprising the reaction product obtained from reacting valeric acid and glycerol at a molar ratio of between 1:0.8 and 1:1.2, for use in prevention and/or alleviation of necrotic enteritis in the gastric tract of galloanserans, such as chicken or turkey.

According to one embodiment of the present invention, the glycerol ester composition comprises at least 30% by weight of glyceryl monovalerate, below 20% by weight of glyceryl divalerate and below 5% by weight of glyceryl trivalerate.

According to a preferred embodiment of the present invention, the glycerol ester composition comprises at least 40% by weight of glyceryl monovalerate, below 15% by weight of glyceryl divalerate and below 2% by weight of glyceryl trivalerate.

Free valeric acid has an unpleasant smell, which causes handling problems. These problems can be avoided by distributing the valeric acid in the form of glycerol esters. According to one embodiment of the present invention, the amount of free valeric acid in the glycerol ester composition is below 0.5% by weight, preferably below 0.1% by weight. Keeping down the amount of free valeric acid also ensures that the pH in the glycerol ester composition is kept at a level where the glycerol ester will not undergo hydrolyzation into glycerol and free acid, hence, the product is kept stable.

According to one embodiment of the present invention the glycerol ester composition is adsorbed on an inert carrier, such as a silica carrier. This allows the composition to be distributed as a dry product. Such a silica carrier preferably comprises porous silica particles with an average particle size of 20-70 μm. According to one embodiment of the present invention, the glycerol ester composition is adsorbed on silica particles in a weight ratio of 50-80% glycerol ester and 20-50% silica particles. Distributing the glycerol ester composition adsorbed on a silica carrier contributes to keeping down the water amount in the composition and thereby inhibiting the hydrolyzation of glycerol ester into glycerol and free acid. The product is kept more stable and the odor problems associated with free valeric acid are minimized The glycerol ester composition according to the present invention can be added to any commercially available feedstuffs for galloanserans. The glycerol ester composition may be incorporated directly into commercially available feeds or fed supplementary to commercially available feeds. The glycerol ester composition according to the present invention can also be added to the drinking water.

According to one embodiment of the present invention the amount of glycerol ester composition fed to the galloanserans is from 0.01 to 1.0% by weight and preferably from 0.05 to 0.7% by weight of the galloanserans' daily feed ration.

EMBODIMENT EXAMPLES

Example 1: In Vitro Experiment on the Antimicrobial Effect of Some Short Chain Fatty Acids and Their Respective Monoglycerides on *Clostridia perfringens*.

MIC (minimum inhibitory concentration) values towards *Clostridia perfringens* were determined for valeric acid, propionic acid and butyric acid, as well as for the corresponding glycerol monoesters of these acids. The results can be seen in Table 1 below.

TABLE 1

| *Clostridia perfringens* | MIC (mmol) |
|---|---|
| Valeric acid | 15 |
| Propionic acid | 62 |
| Butyric acid | 62 |
| Glyceryl monovalerate | 15 |
| Glyceryl monopropionate | 250 |
| Glyceryl monobutyrate | 125 |

It can be seen in Table 1 that valeric acid is more effective against *Clostridium perfringens* than either propionic acid or butyric acid. What is very interesting to note is that the low inhibitory concentration of valeric acid needed against *Clostridium perfringens* is retained also when the monoester of valeric acid is used. In the case of propionic acid, the MIC is four times higher for the monoester compared to the free acid. With butyric acid, the MIC is doubled for the monoester compared to the free acid. This makes glyceryl monovalerate an excellent alternative for reducing and/or inhibiting gram-positive bacteria like *Clostridium perfringens*.

Example 2: In Vivo Experiment: Use of Glyceryl Monovalerate to Control *Clostridium perfringens*-Induced Necrotic Enteritis in Broiler Chicken The effect of glyceryl monovalerate on *Clostridia perfringens*-induced necrotic enteritis in broiler chicken was investigated.

Bacterial Strains and Vaccines

The challenge strain used in the in vivo trials, *C. perfringens*, was isolated from the gut of a broiler chicken with necrotic lesions from a flock with weight gain problems. The strain was classified as a type A strain (netB positive, beta-2 and enterotoxin negative).

For inoculation, the strain was grown for 12 (one day) or 6 h in Brain Heart Infusion broth (BHI, Oxoid, Basingstoke, England).

A ten-fold dose of the anticoccidial vaccine Paracox®—5 (Schering-Plough Animal Health, Brussels, Belgium), containing live, attenuated oocysts of *Eimeria (E.) acervulina, E. maxima* (two lines), *E. mitis* and *E. tenella* was used in this study.

Nobilis Gumboro D 78 vaccine (Schering-Plough Animal Health, Brussels, Belgium) was given in the drinking water.

Animals and Housing

In this experiment, 132 one-day-old Ross 308 broilers of mixed sex, from a commercial hatchery, were divided in cages of 2 m², 33 birds per treatment group. Before the trial, all rooms were decontaminated with Metatectyl® (Clim'oMedic) and with a commercial anticoccidial disinfectant (Bi-OO-cyst®; Biolink Ltd, York, UK). The birds were given drinking water and feed ad libitum. A 23 h/1 h light darkness program was applied.

Experimental Study Design:

The first 7 days, the chickens were fed a starter diet and from day 8 until 15, a grower diet. Both the starter and the grower diet were a wheat/rye (43%/7.5%) based diet, with soybean meal as protein source. From day 17 onwards, the same diet was used with the exception that fishmeal (30%) was used as a protein source. The feed was provided by the Institute for Agricultural and Fisheries Research (ILVO). The tested products were mixed in the feed. The Gumboro vaccine was given in the drinking water at day 16 in all groups. All groups were challenged orally three times a day (8.00 h; 14.00 h, 20.00 h) with approximately $5.10^8$ cfu *C. perfringens* strain 56 at days 17, 18, 19 and 20. At day 18 all birds were orally inoculated with a ten-fold dose of Paracox-5™. At day 21 all animals were euthanized by intravenous sodium pentobarbital injection.

Model:

TABLE 2

Time schedule for the in vivo study.

| | d 16 | d 17 | d 18 | d 19 | d 20 | d 21 |
|---|---|---|---|---|---|---|
| Gumboro | x | | | | | |
| Feed + fishmeal | | x | x | x | x | x |
| Inoculation *C. perfringens* (8-14-20) | | x | x | x | x | |
| Paracox ® x10 | | | x | | | |
| Scoring | | | | | | x |

Products Tested:

Group 1: negative control (no challenge with *C. perfringens*)

Group 2: positive control

Group 3: glyceryl monovalerate at the lower concentration (adsorbed on a silica carrier)

Group 4: glyceryl monovalerate at the higher concentration(adsorbed on a silica carrier)

Glyceryl monovalerate was added to the feed in two different concentration series shown in Table 3 below:

TABLE 3

Concentrations of products added to the feed (kg/ton)

| | Glyceryl monovalerate, on silica carrier low conc | Glyceryl monovalerate, on silica carrier high conc |
|---|---|---|
| Week 1 | 2.5 | 5 |
| Week 2 | 2 | 2.5 |
| Week 3 | 1.5 | 2 |

Intestinal lesions in the small intestine (duodenum to ileum) were scored blinded as follows:

0: no gross lesions

1: congested intestinal mucosa

2: small focal necrosis or ulceration (1-5 foci)

3: focal necrosis or ulceration (5-16 foci)

4: focal necrosis or ulceration (16 or more foci)

5: patches of necrosis 2-3 cm long

6: diffuse necrosis typical of field cases

Lesion scores of 2 or more were classified as necrotic enteritis positive

Statistical Analysis

The GraphPad Prism Software, Inc was used to determine whether there were significant differences between groups. Statistical significance was determined at a P value of <0.05.

Results

The results are presented in the FIGURE, which shows the percentages of birds in each group with macroscopic lesion score ≥2.

Glyceryl monovalerate at the lower concentration gave the best results with 27% of the animals within the group diagnosed as necrotic enteritis positive. This is a significant improvement compared to the positive control group (no glyceryl monovalerate added to the feed), where 71% of the animals were diagnosed as necrotic enteritis positive.

The invention claimed is:

1. A method for reducing and/or inhibiting growth of gram-positive, pathogenic bacteria in animals, the method comprising administering to the animals a glycerol ester composition obtained or obtainable from reacting valeric acid and glycerol at a molar ratio of between 1:0.8 and 1:1.2; wherein the gram-positive, pathogenic bacteria comprises *Clostridium perfringens* and wherein the glycerol ester composition comprises at least 40% by weight of glyceryl monovalerate.

2. The method of claim 1, wherein the animals are galloanserans and the method alleviates necrotic enteritis in the gastric tract of the galloanserans.

3. The method of claim 2, wherein the necrotic enteritis is caused by *Clostridium perfringens*.

4. The method of claim 2, wherein the galloanserans are galliformes.

5. The method of claim 2, wherein the galloanserans are anseriforms.

6. The method of claim 2, wherein the glycerol ester composition is fed to the galloanserans in an amount between 0.01 to 1.0% by weight of the galloanserans' daily feed ration.

7. The method of claim 2, wherein the glycerol ester composition is fed to the galloanserans in an amount between 0.05 to 0.7% by weight of the galloanserans' daily feed ration.

8. The method of claim 1, wherein the glycerol ester composition is adsorbed on a carrier as a dry product.

9. The method of claim 8, wherein the carrier is a silica carrier.

10. The method of claim 1, wherein the compositions includes at least 1.5 fold more glyceryl monovalerate than glyceryl divalerate and at least 8 fold more glyceryl monovalerate than glyceryl trivalerate.

11. A method for reducing and/or inhibiting necrotic enteritis in galloanserans caused by *Clostridium perfringens*, the method comprising administering to the galloanserans a glycerol ester composition obtained or obtainable from reacting valeric acid and glycerol at a molar ratio of between 1:0.8 and 1:1.2, wherein the glyceryl ester composition comprises at least 40% by weight of glyceryl monovalerate.

12. The method of claim 11, wherein the compositions includes at least 1.5 fold more glyceryl monovalerate than glyceryl divalerate and at least 8 fold more glyceryl monovalerate than glyceryl trivalerate.

* * * * *